United States Patent
DeVincenzo et al.

[11] Patent Number: 5,853,291
[45] Date of Patent: Dec. 29, 1998

[54] SUBPERIOSTEAL BONE ANCHOR

[76] Inventors: John DeVincenzo, 1312 Garden St.;
Steven Prins, 826 Alyssum Ct., both of San Luis Obispo, Calif. 93401

[21] Appl. No.: 948,731

[22] Filed: Oct. 10, 1997

[51] Int. Cl.⁶ .................................................. A61C 8/00
[52] U.S. Cl. ............................................ 433/176; 433/18
[58] Field of Search .............................. 433/176, 17, 18, 433/19, 21, 22; 623/16, 18, 20

[56] References Cited

U.S. PATENT DOCUMENTS

| | | | |
|---|---|---|---|
| 3,302,288 | 2/1967 | Tepper | 433/17 |
| 3,798,773 | 3/1974 | Northcutt | 433/19 |
| 4,795,342 | 1/1989 | Jones | 433/22 |
| 5,052,930 | 10/1991 | Lodde et al. | 433/176 |
| 5,163,961 | 11/1992 | Harwin | 623/23 |
| 5,538,427 | 7/1996 | Hoffman et al. | 433/173 |
| 5,562,445 | 10/1996 | DeVincenzo et al. | 433/18 |

FOREIGN PATENT DOCUMENTS 2631813  12/1989  France ................................. 433/176

*Primary Examiner*—John J. Wilson
*Attorney, Agent, or Firm*—James B. Middleton

[57] ABSTRACT

A subperiosteal bone anchor has a base that is thin and moldable so the base can be conformed to bone where it is to be placed. The base is formed as a plurality of arms, and leaves with central holes in the leaves so screws can urge the leaves against the bone. The edges of the base are scalloped, and very thin to facilitate bone overgrowth. Central to the arms is a stem extending up, and having a variety of connection mechanisms for attachment of orthodontic appliances.

11 Claims, 5 Drawing Sheets

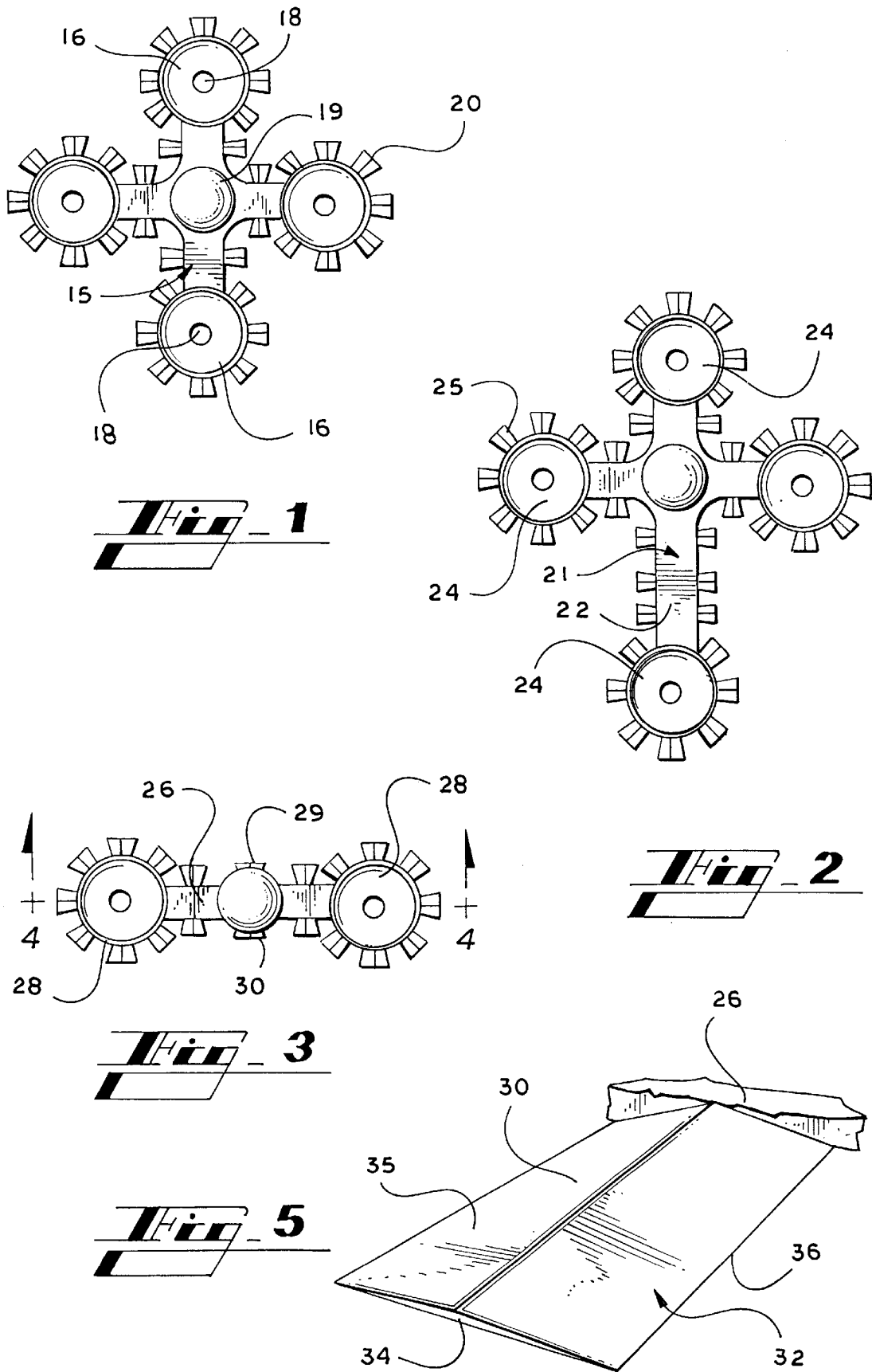

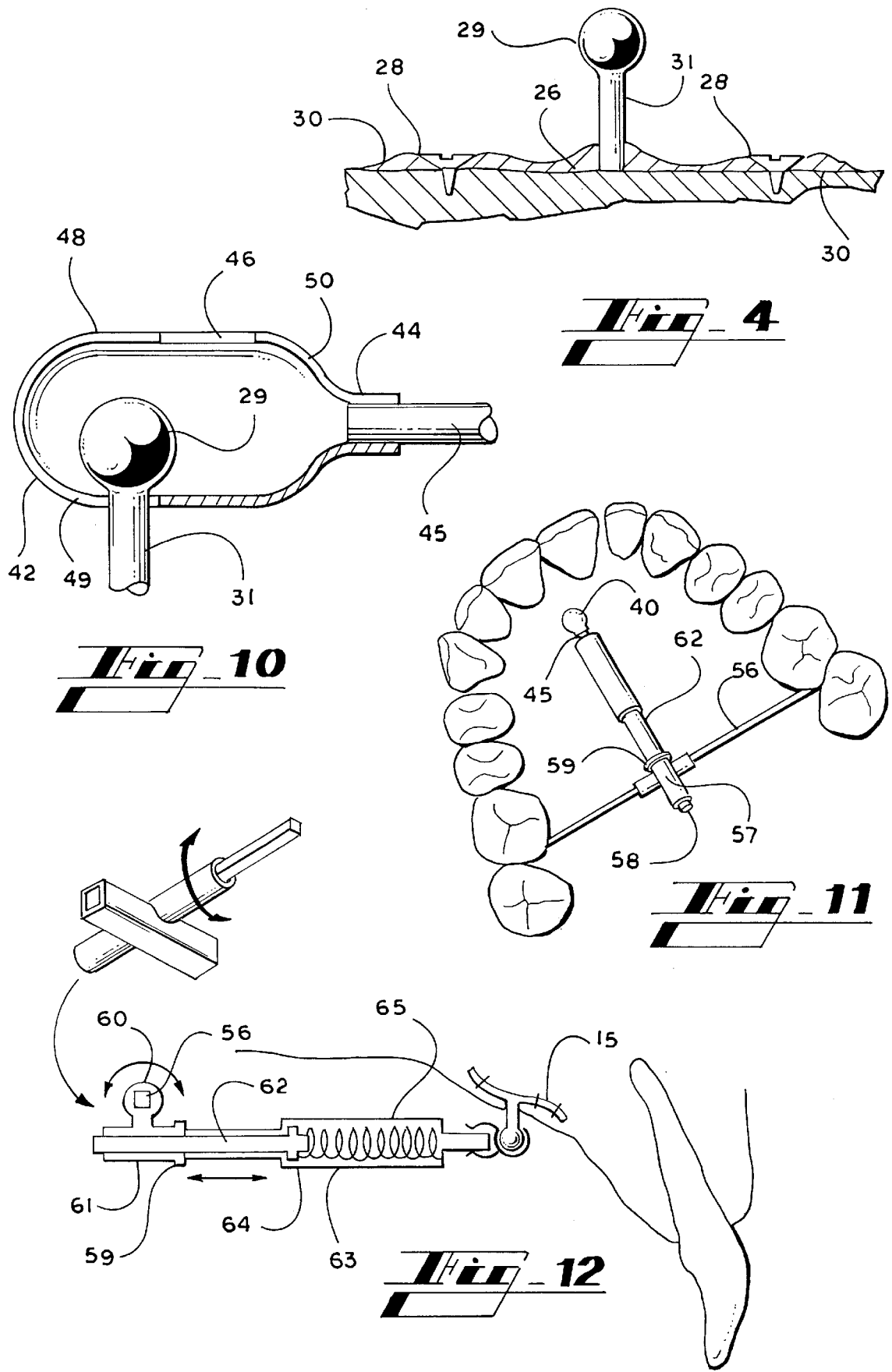

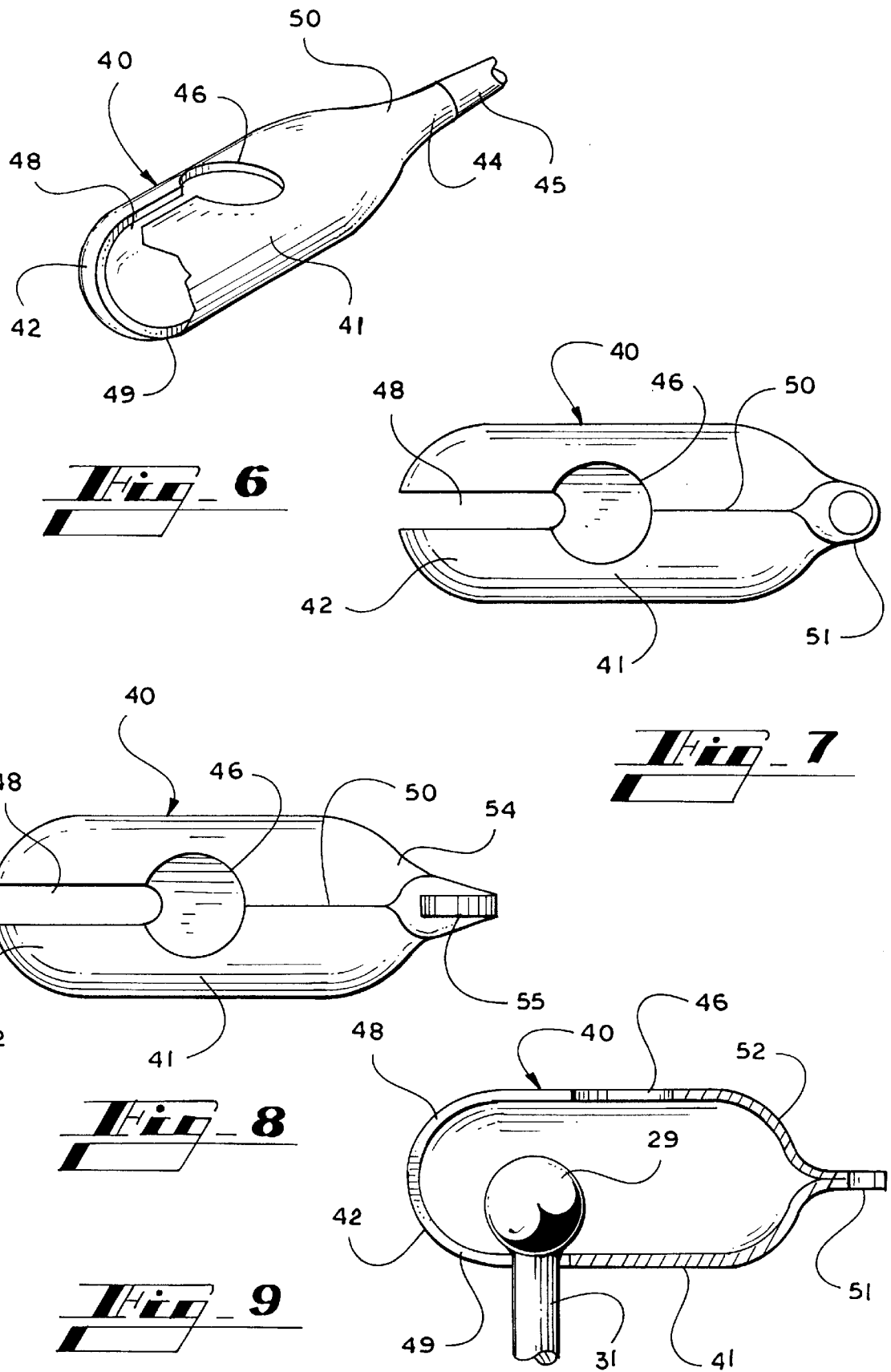

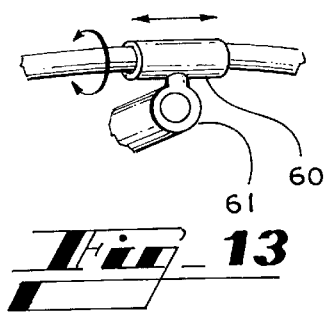
Fig_13
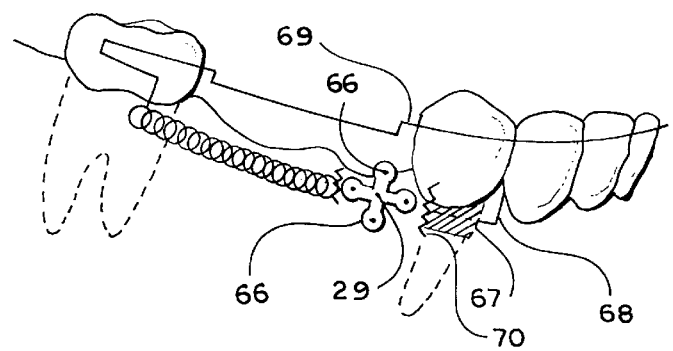
Fig_15
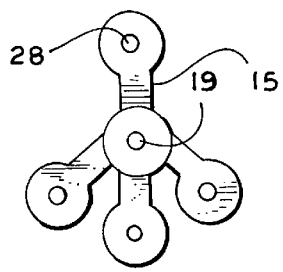
Fig_14
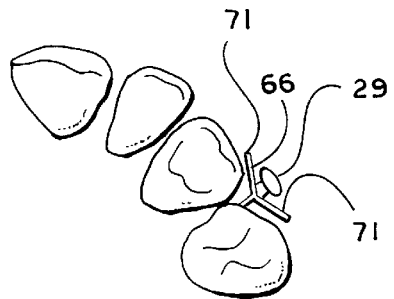
Fig_17
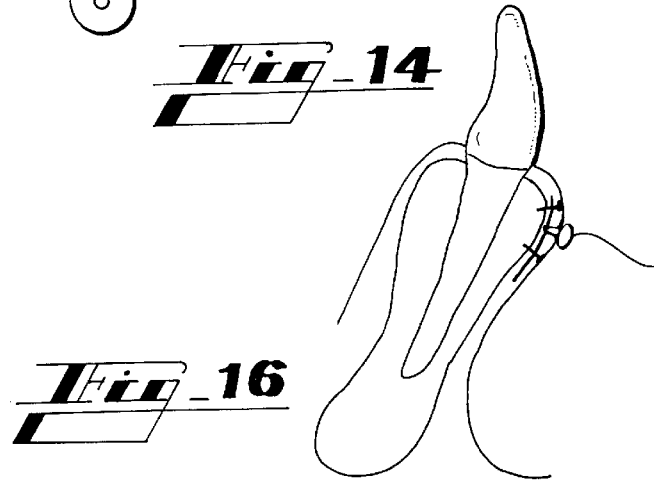
Fig_16
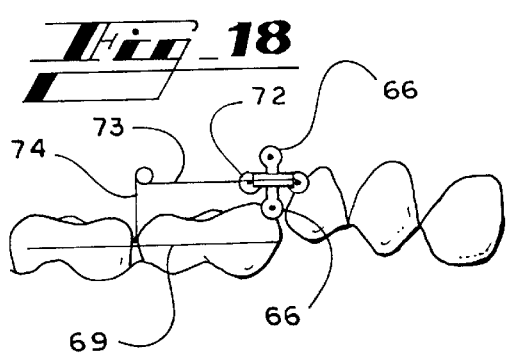
Fig_18
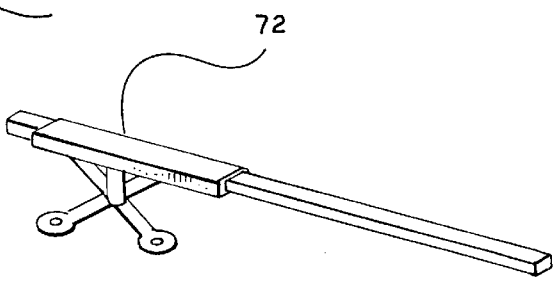
Fig_19

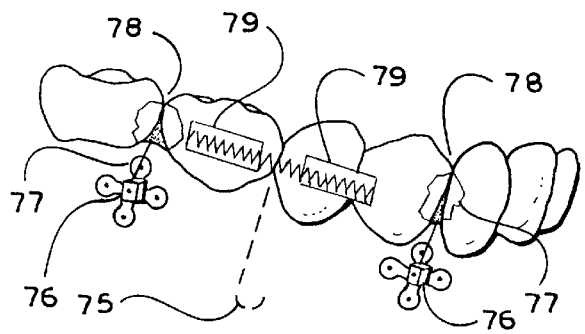
Fig_20
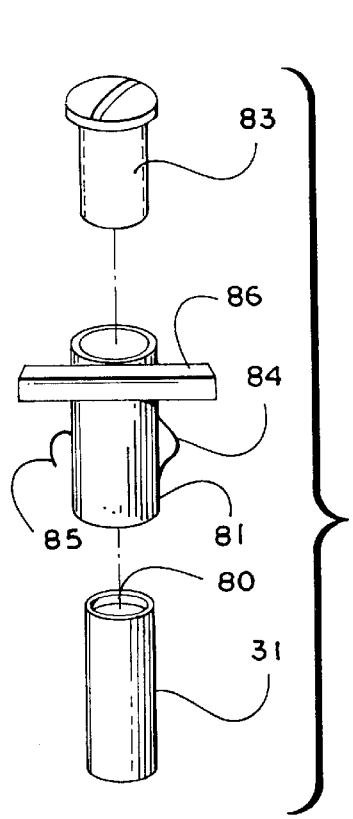
Fig_21
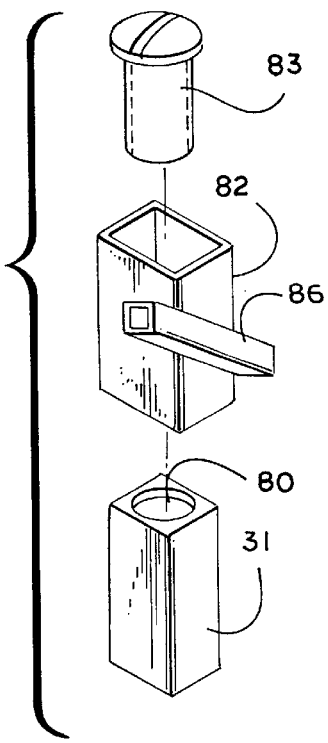
Fig_22
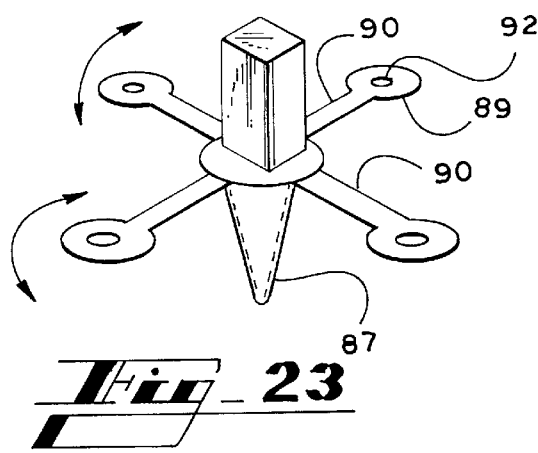
Fig_23
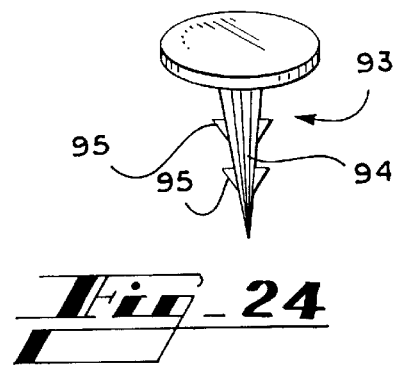
Fig_24

SUBPERIOSTEAL BONE ANCHOR

BACKGROUND OF THE INVENTION

1. Field of the Invention

This invention relates generally to orthodontic appliances, and is more particularly concerned with a miniature subperiosteal bone anchor usable as a fixed pushing or pulling point for moving a patient's teeth.

1. Discussion of the Prior Art

The concept of implants as a tool to be used in orthodontic treatment has been addressed with various levels of sophistication and clinical adaptation for 20 years. Sherman (Am. J. Orthod. 74:79,1978) had some success using endosteal vitreous carbon implants in dogs while Smith (Am. J. Orthod. 76:618,1979) reported increased success using bioglass-coated aluminum oxide endosteal implants in monkeys. A few years later Creekmore (J. Clin. Orthod. 17:266, 1983) reported clinical success in humans using a titanium screw as an endosteal implant and since then Roberts (J. Clin. Orthod. 18:693,1994) and Turley (Angle Orthod. 58:151,1988) have published numerous articles on endosteal implants and demonstrated their clinical usefulness.

More recently Block and Hoffman first patented (Block, Orthodontic Anchor U.S. Pat. No. 5,066,224, 1991; Hoffman, Subperiosteal Bone Anchor, U.S. Pat. No. 5,538, 427, 1996) then later published (Am. J. Orthod. Dentofac. Orthop. 107:251,1995) an orthodontic anchorage system that did not penetrate the bone as endosteal implants do but merely rested on the surface of the bone. They called this subperiosteal bone anchor an onplant. They noted that osseointegration occurred on the under-surface onplant and thus patented the under-surface texture and configuration of the onplant.

Subperiostal bone anchors have been known and used in dentistry for many years and their value in orthodontics apparent since at least the mid 1980's (Turley, J. Dent. Res. 63A:334, 1984). But it is to the credit of Block & Hoffman, utilizing their onplant, that a clinical useful orthodontic anchor system has been developed based on the observation of osseointegration on the under-surface of the onplant, that is between the onplant and the bone upon which it rests.

One of the difficulties with the prior art is that the device is rigid and thick and cannot be molded, at the time of the surgery, to the unique bone morphology found at each surgical site. This thickness is necessary to provide the needed roughened under surface with sufficient bulk for mechanical locking with bone. Further, the bone-anchor interface surface is very complex, being shaped to allow bone ingrowth. Thus, a complex, machined or cast surface must be shaped individually to conform to each unique bone conformation, all of which requires prior impressions, and/ or x-ray scans or the like. Even after the prior art has osseointegrated, a further surgical procedure is necessary to uncover a portion of the anchor and attach an extruding abutment. It is, then, the abutment that is fixed to various appliances for moving teeth as desired.

It will therefore be understood that the prior onplants are very rigid, cannot be adapted to irregular bony contours at the time of surgery, are somewhat bulky and thus limited to intraoral placement only in locations where overlying soft tissue is relatively thick, such as in the palate, and require two separate surgical procedures. Additionally the attachment procedure connecting the onplant to teeth is complex and requires additional laboratory steps.

SUMMARY OF THE INVENTION

The present invention provides a miniature stemplant where in the base is extremely thin and somewhat malleable so it can be shaped at the time of surgery to conform to the unique bone morphology found at any particular site. Screws or nails are used to force the leaves of the stemplant down against the bone, to stabilize it during osseointegration and to provide additional anchorage. The base of the stemplant is quite thin, allowing the flexibility mentioned above, while encouraging overgrowth of bone. The stemplant does not use the undersurface bone-metal interface for stabilization but relies on overgrowth of bone from the margins to finish the needed anchorage. Furthermore, the edges of the base are scalloped and sloping to increase the length of the periphery, to increase the surface area and to facilitate overgrowth of bone onto the top surface.

The configuration of the stemplant can be viewed as a 2,3 or 4 leaf clover radiating from a central "stem". This unique configuration can withstand the torquing and dislodging forces that will be generated through the "stem" much better than the single, thick, rigid base of the prior art onplant. This stem is fixed to the base of the stemplant of the present invention, the end of the stem having an enlarged sphere. A plurality of attachment means is provided for quick and easy attachment of various orthodontic appliances to this spherical end. The sphere protrudes out of the epithelium or mucous membrane at the time of installation of the stemplant, so appliances can be attached without further surgery.

BRIEF DESCRIPTION OF THE DRAWINGS

These and other features and advantages of the present invention will become apparent from consideration of the following specification when taken in conjunction with the accompanying drawings in which:

FIG. 1 is a top plan view of a miniature stemplant made in accordance with the present invention;

FIG. 2 is a view similar to FIG. 1 but showing another modified form thereof;

FIG. 3 is a view similar to FIG. 1 but showing another modified form thereof;

FIG. 4 is an enlarged, cross-sectional view taken along the line 4—4 in FIG. 3;

FIG. 5 is a fragmentary perspective view showing a portion of the scalloped edge of the base of the device of the present invention;

FIG. 6 is a perspective view, partially broken away, showing an attachment means for use with the stemplants shown in FIGS. 1–3;

FIG. 7 is a top plan view of a modified form of attachment for use with the pinplant of the present invention;

FIG. 8 is a top plan view of another modified form of attachment means;

FIG. 9 is a longitudinal cross-sectional view of the device shown in FIG. 7; and, FIG. 10 is a longitudinal cross-sectional view of the device shown in FIG. 6.

FIG. 11 is a perspective view showing the means of distalizing the molars by pushing from the stemplant.

FIG. 12 is an enlarged cross-sectional view of FIG. 11 and illustrates the positioning of the adjustable cylinder assembly and the functioning and structure of the distalizing apparatus.

FIG. 13 is yet another view of the adjustable cylinder assembly.

FIG. 14 is a plan view of another modification of the 4 leaf stemplant when more anchorage is needed at the posterior end.

FIG. 15 is a perspective view showing how the stemplant can be used to pull posterior teeth forward or push anterior teeth forward.

FIG. 16 is a cross-sectional view showing the irregular bony contours encountered in this region and thereby illustrating the importance of contouring the anchor.

FIG. 17 is a perspective top view illustrating again the importance of moldability at the time of insertions.

FIG. 18 is a side view showing the stemplant use in intruding selected teeth.

FIG. 19 is a perspective view of the stemplant of FIG. 18 in which a tubular head is substituted for the ball of FIG. 1.

FIG. 20 is a perspective view utilizing the stemplants to stabilize the dentition in conjunction with distraction osteogenesis.

FIG. 21 is an exploded perspective view utilizing a hollow stem, a sleeve carrying various adjustable attachments and screw cap.

FIG. 22 is similar to FIG. 21 except the stem is angular instead of cylindrical.

FIG. 23 is a perspective view of a modification of the stemplant in which the opposite end of the stem serves as a major screw while one or more leaves can be either nailed or screwed onto bone.

FIG. 24 is a perspective view of the bone nail which can be used to secure one or more leaves.

DETAILED DESCRIPTION OF THE EMBODIMENTS

Referring now more particularly to the drawings, and to those embodiments of the invention here presented by way of illustration, FIG. 1 illustrates a stemplant having a base 15 in the form of an equilateral cross. At the end of each of the four arms of the cross is a screw receiving member called a leaf 16. As will be discussed in more detail hereinafter, each leaf 16 is adapted to receive a flat head screw or nail, the head of which will be flush with the upper surface of the leaf 16. At the center of each leaf 16 there is a hole 18 to receive the shank of the screw or nail. It is understood that some of the leaves may not have the hole 18 and not be screw or nail receiving leaves.

Centrally of the base 15, there is an upstanding stem carrying a ball 19 at its uppermost end. This will be discussed in more detail later.

It is important to notice that the entire base 15 and leaves 16 have their edges scalloped, as indicated at 20. Since one intent of the stemplant of the present invention is to encourage overgrowth of bone, the scalloped edge is important to yield a very long periphery for great bone overgrowth.

FIG. 2 shows a stemplant similar to FIG. 1, but having a base 21 that has one longer arm 22. Although in this Fig. there is a screw or nail receiving leaf 24 at the end of each of the arms of the base 21 usually only 2 of the leaves have holes for screws or nails and, all edges of the base are scalloped as indicated at 25. The purpose of FIG. 2 is to show that the base of the stemplant does not have to be equilateral, but can take any shape desired including changes in lengths and/or angles to fit in various locations within a patient's mouth.

FIG. 3 shows yet another modification of the stemplant shown in FIG. 1, the device of FIG. 3 having a base 26 having only two leaves. Each of the two leaves terminated in a screw or nail receiving member 28, and a stem carrying a ball 29 at its upper end is attached to the center of the base 26. Again, the periphery of the base 26 is scalloped as at 30. Three leaf configurations as well as two leaf boomerang shapes can be envisioned also.

Attention is now directed to FIG. 4 of the drawings for a better understanding of the construction of the stemplants shown in FIGS. 1–3. While FIG. 4 is indicated as a cross-sectional view through FIG. 3, it should be understood that a cross-section through the two transverse leaves of FIG. 1 or FIG. 2 would look precisely the same. However, reference will be made only to FIGS. 3 and 4, and it will be understood that the same construction applies to FIGS. 1 and 2.

The base 26 is generally flat, but varying in thickness and is preferably quite thin in the arms that connect leaves to the stem. The base 26 merges with the screw or nail receiving leaves 28, and the scallops 30 make up the periphery of the leaves 28. While the base varies in thickness somewhat the scallops 30 begin at about the same thickness as the base 26, then taper down to an extremely thin edge, perhaps to a knife edge to facilitate osseointegration by the bone growing over the top and around the edges of the stemplant.

Between the leaves of the base 26 is a stem 31 which carries the ball 29. The stem 31 may be fixed to the base 26 in any way desired, but the stem 31 should be rigidly fixed to the base 26, as by soldering, welding, threading, or the like. The length of the stem 31 is variable to suit one's needs, but it is contemplated that the stem 31 will be long enough to project through the soft tissue after surgical installation of the stemplant to dispose the ball 29 above this soft tissue.

Those skilled in the art should understand that the directions such as top, bottom, up down etc. are relative to the bone on which the device is being mounted. The bone is always at the bottom, and "up" is away from the bone and "down" is towards the bone. The anchors, or stemplants, of the present invention may be mounted in any direction with respect to the earth, so the above mentioned directions are used for clarity of description.

Looking briefly at FIG. 5 of the drawings, one of the scallops comprising the scalloped edge 30 is shown. Here it can be seen that the scallop 32 is substantially as thick as the base 26 at its emergence, but tapers in all directions to thinner edges. So, in FIG. 5, the scallop 32 tapers in the longitudinal direction to a very thin edge at the extending end 34. At the same time, the scallop tapers transversely of the scallop so the two lateral edges 34 and 36 are substantially knife edges.

In view of the construction of the stemplant as described above and shown in FIGS. 1–5 of the drawings, it will be understood by those skilled in the art that the stemplant of the present invention will be placed against the bone in the selected location. As the device is placed, the base 15, 21 etc. will be bent to conform to the shape of the surface wherever the device is to be installed. Further, one or more screws or nails will be passed through the leaves 16, 24, or 28, and these will pull the leaves down more firmly against the bone. The periosteum and other soft tissues will then be closed over the base of the device, while the stem 31 protrudes through the membrane to position the ball 29 outside. As a result, when the tissue heals and enough time has passed to have osseointegration, the stemplant is ready for utilization with an orthodontic appliance without the need for a second surgical procedure to expose the protruding part.

To encourage bone growth over the leaves and base of the stemplant the top surface of said leaves and base may be coated with an osseointegratable material such as hydroxyapatite.

One of the important features of the present invention is the simplicity of attachment of an orthodontic appliance to the stem of the stemplant. Although a number of attachment means and stem configurations are an integral part of this patent and will be described later, the attachment means shown in FIG. 6, with slight variations shown in FIGS. 7–10 has the broadest application. In all of FIGS. 6–10 the means for attachments to the stemplant is the same, and the variation is in the means for connection to an orthodontic appliance.

Looking specifically at FIG. 6 of the drawings, the attachment means 40 comprises an elongated body 41 that is generally cylindrical. One end of the body 41 is hemispherical as shown at 42, while the opposite end of the body 41 tapers down to a smaller diameter at 44 to receive an end of an orthodontic appliance 45 such as a steel rod. While numerous appliances may be fixed to the end 44, the device here shown is a modification of the plunger end of the "Resiliently Expandable Orthodontic Device" as disclosed in U.S. Pat. No. 5,562,445. The present invention provides an excellent mounting for one end of the spring disclosed and claimed in that patent.

It will be noticed that the body 41 defines a generally circular hole 46 in its upper surface. A slot 48, then, extends from the hole 46, around the spherical end 42, and into the bottom surface 49 of the body 41. There is a narrow slit 50 in the upper surface extending across the end 44. Those skilled in the art will understand that this slit 50 results from creation of the attachment means by forming it from sheet material. Other embodiments of the invention may not have the slit 50.

Turning to FIGS. 7 and 9 of the drawings, another attachment means 40 is shown. Since the device in FIGS. 7 and 9 is substantially the same as FIG. 6, the same numerals are used for the same parts. The only difference is in the connection to an orthodontic appliance, so these parts carry different numerals. In FIGS. 7 and 9, rather than the smaller cylinder 44, into which fits the shaft 45, the connection means includes a horizontally disposed ring 51, the end of the body 41 tapering down to dispose the ring 51 generally centrally of the cylindrical body 41. The ring 51 can then receive ligature wires or other connecting means for an orthodontic appliance.

FIG. 8 show another embodiment of the connection means 40, and the device in FIG. 8 again carries the same reference numerals as FIG. 6 for equivalent parts. The device of FIG. 8 also has a tapering end 54, the end 54 terminating in a vertically disposed, open ring 55. Those skilled in the art will recognize that the open ring 55 is for attaching elastics.

The attachment shown in FIG. 10 is the same as in FIG. 6 except from a different perspective.

It should therefore be quickly understood that numerous connections can be made to orthodontic appliances using the attachment means of the present invention.

In view of the foregoing description, and referring to FIGS. 9 and 10 of the drawings, it will be understood that, to connect the attachment means 40 to the stem 31 and ball 29, one simply inverts the attachment means 40 so the ball 29 can pass through the hole 46. The device 40 is then moved so the stem 31 passes through the slot 48 while the device is rotated to its up-right position. In its upright position as shown in FIGS. 9 and 10, it will be seen that, if a force is exerted to the left as viewed in these figures, the slot 48 will act against the stem 31 to limit the motion. Conversely, if a force is exerted to the right as viewed in these figures, the ball 29 will abut the spherical end 42 to limit the motion. The attachment means 40 can therefore be used to exert a force in either direction desired. It will of course be remembered that the stemplant is solidly fixed to the bone and can be a point for exerting forces in any direction.

Thus, the present invention provides a stemplant easily fixable to the bone of a patient, and placed underneath the soft tissues of the oral cavity. The leaves are bent at the time of surgery to conform to the receiving bone, which are then preferably screwed or nailed down to pull the device firmly against the bone. A stem extends through the soft tissues and carries a ball or other enlargement on the extending end. After the tissue heals, and there has been time for osseointegration, an attachment means can be easily slipped over the stem and its ball, and any desired orthodontic appliance can be connected to the attachment means.

The procedure used to distalize the entire maxillary dentition, using a single stemplant placed at the anterior aspect of the floor of the palate is described. After osseointegration of the stemplant a prior art transpalatal stabilizing bar 56, is attached to the molars. Prior to this attachment to the molars an appropriately sized, adjustable cylinder assembly 57 has been inserted, at approximately the midline of the palate, on this transpalatal stabilizing bar FIG. 11. This stemplant can be connected to the adjustable cylinder assembly in a number of ways with that means depicted in FIG. 6 preferred. The opposite end 58 prevents further passage. The distalizing apparatus which attaches to the stemplant at the more anterior end and the adjustable cylinder assembly at the posterior end is a modification of the plunger end of U.S. Pat. No. 5,562,445 and is illustrated in FIG. 12.

The adjustable cylinder assembly 57 actually consists of two perpendicularly mounted cylinders FIG. 11, 12, 13. A laterally mounted cylinder 60 permits side to side as well as rotational adjustment FIG. 13 while the sagitally mounted cylinder 61 serves a guide to assure translational distalization of the molars. By moving the adjustable cylinder assembly along the transpalatal stabilizing bar differential forces can be applied to the molars. If distalization of only one molar is desired the transpalatal bar is not used but rather a unilateral extension from the molar to be moved is attached into the cylinder 60. When desired adjustments have been made in the adjustable cylinder assembly 57 the lateral cylinder 60 can either be crimped on the transpalatal bar or filled with material to prevent additional movements.

When the molars or other teeth have been moved sufficiently by the distalizing apparatus further movement of the ram 62 can be prevented by either tying the ram at its top 59 to the anterior bar or by injecting the ram housing 63 with material which hardens with time 64 & 65.

When the stemplant is used for this purpose, that is to distalize the maxillary dentition and/or molars the base configuration should be modified, as shown in FIG. 14, to reflect the additional load-bearing area needed in the posterior region of the stemplant.

The adjustable cylinder assembly 57 can be modified in shape to resemble a "T" and positioned in the same plane as the lateral cylinder. For some patients this would be more comfortable as no projections would occur either vertical or posterior to the plane of the stabilizing bar 56.

The procedure used to move the maxillary posterior teeth anteriorly, such as in partial anodontia, utilizing a single palatal stemplant, would be similar to that just described except that the spring in the ram housing 63 would be closed coil wound and hence under tension instead of under compression when activated. A tie would hold the ram stop 59 to the adjustable cylinder assembly 57.

One of the most significant advantages of the thin-based, moldable stemplant over the thick based, rigid onplant is the great versatility in placement in virtually any area of the mouth. In no location is this advantage more apparent than in the thinly covered and irregularly contoured bone in the buccal regions of the mandibular and maxillary cuspids and first bicuspids.

An example of a buccally placed stemplant in this region will be described. In FIG. 15 the mandibular first and second molars and bicuspids are missing. The screws or nails 66 are placed in the vertical plane only while the attachment means 40 would be as shown in FIG. 8 or 9 if a closed coil spring elastomeric thread or tubing were used to move the molar anteriorly.

There are times when it is desirable to push one or more teeth anteriorly. Referring again to FIG. 15 and proposing the example of desiring to move all the mandibular anterior teeth forward the attachment means 40 as illustrated in FIG. 6 would be used. By converting the solid shaft 45 into a tubular shaft 67 and using a wire extension 68 either attached to the archwire 69 or to the cuspid bracket (not shown), which has a 90° bend 70 and is placed in the arbor space (inside diameter space) of the open coil spring contained within the tubular shaft 67, anterior movement would be accomplished.

FIGS. 16 & 17 are intended to show the irregular bony contours in this region and to help visualize the importance of moldability of the stemplant so it can adapt to the various bony configurations in the mouth. The stemplant of FIG. 2 would be used in this region while it is clear from FIG. 17 that no screws or nails could be placed in the horizontal receiving leaves 16 and 71.

There are times when one or more teeth have extruded because of a lack of tooth or teeth contact from the opposing arch. When this occurs it is presently nearly impossible to intrude the tooth or teeth back to their desired positions(s). The stemplant can accomplish such movement and the following example will serve to illustrate this.

In FIG. 18 can be seen the extrusion of both maxillary molars. A stemplant is inserted between the first molar and the second bicuspid and attached into bone 66. Instead of a sphere projecting from the stem a rectangular tube 72 is attached through which rectangular wire passes. The attachment 74 of the rectangular wire 73 to the arch wire 69 will create an intrusive force to the molars. Many intrusions can be accomplished with rough wires and cylindrical tubes but if torquing forces are also desired or needed rectangular tubes and wires should be used.

FIG. 19 is an enlargement of the rectangular attachment to the pin instead of the spherical attachment presented in all the previous figures.

While much of the work orthodontists do involves the movement of teeth there are some conditions where the size of one jaw bone is smaller or shorter than desirable. When this condition occurs the stemplant can give the orthodontist/ surgeon team another tool by which to accomplish their goals.

Distraction osteogenesis is a process by which a bone can be increased in length by stimulating bone formation in a region other than at its growth centers. Some 40 years ago Gavrile Ilizarov rekindled interest in this procedure and was the first of the modem clinicians to develop techniques to accomplish this. Since his pioneering work distraction osteogenesis has been performed in many clinics throughout the world and is now just beginning to be done on the bones of the face. The stemplant can be used during intraoral distraction osteogenesis and has particular application for the correction of severe class II malocclusions.

Five to six months prior to the circumferential corticotomy 75 four stemplants would be placed on the buccal, mesial and distal of the corticotomy sites as shown in FIG. 20. Attached to the extruding stem is a vertically positioned rectangular or round tube 76 through which an appropriate size wire may be inserted 77 at one end and attached at the other either into the jackscrew appliance 79 or directly to the teeth. The use of the stemplant with a vertically positioned tube for its head is similar to the horizontally positioned tube of FIG. 19.

Thus, it can be apparent that it is the intention of this patent to have a great variety of "heads" at the extruding end of the stemplant and several shapes and configurations have been presented to illustrate this versatility.

Another modification of the stemplant is depicted in FIG. 23. A single endosseous screw 87 is used as the stabilizing mechanism said screw being an integral part of the stem 88. Radiating out from the base of the stem are several, here depicted as 4, leaves 89 as described previously herein. The arms 90 connecting the stem to the leaves are bent upward while screwing the stemplant into the bone and are thereafter bent downward to assure close proximity to the underlying bone as illustrated by the arrows 91. At the center of each leaf may be a tapered hole 92 into which bone may grow and as described previously in this patent into which one or more of the previously mentioned screws or nails may be placed for additional osseointegration and stability.

In FIG. 24 is illustrated a power driven nail 93 which can be forced into the bone fitting into the hole 92. Vertical grooves 94 in this nail along with projections 95 aid in retention and stability and afford increased surface area for osseointegration.

The use of coating such as hydroxyapatite over the soft tissue surface and edges of the stemplant are recognized as well as the scratching of the bone on the underside of the stemplant. Both of these procedures can enhance the osseointegration process.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

What is claimed as invention is:

1. A subperiosteal bone anchor for use in conjunction with orthodontic appliances, said bone anchor comprising two or more leaves, narrow arms connecting said leaves, said anchor being adapted to rest directly on bone, said leaves being moldable to the contours of bone on which said anchor is to be placed, the edges of said arms and said leaves including a plurality of scallops therearound.

2. A subperiosteal bone anchor as claimed in claim 1, at least one of said leaves defining a hole centrally thereof for receiving a fastener therethrough.

3. A subperiosteal bone anchor as claimed in claim 1, said anchor including four of said leaves, said narrow arms connecting said leaves being arranged as a cross.

4. A subperiosteal bone anchor as claimed in claim 1, wherein said scallops taper from the thickness of said edges to substantially a knife edge.

5. A subperiosteal bone anchor as claimed in claim 4, said anchor further including attachment means for attaching an orthodontic appliance to said anchor, said attachment means comprising a stem fixed to said arms, and a ball at the upper end of said stem.

6. A subperiosteal bone anchor as claimed in claim 5, and further including connection means for an orthodontic appliance, said connection means comprising a hollow body defining an opening in the tip thereof for receiving said ball therethrough, and a slot in said body communicating with said opening, said slot having a width sufficient to receive said pin and extending around a first end of said body to the bottom of said body, said first end of said body being substantially spherical, and a second end of said body adapted for connection of an orthodontic appliance.

7. A subperiosteal bone anchor as claimed in claim 6, said second end of said body being substantially cylindrical, and having a shaft fixed thereto.

8. A subperiosteal bone anchor as claimed in claim 7 said shaft being attached to a spring housing.

9. A subperiosteal bone anchor as claimed in claim 5, said second end of said hollow body defining an open ring for receiving tension delivering forces or for stabilizing teeth attached to said open ring.

10. A subperiosteal bone anchor as claimed in claim 5, said second end of said hollow body defining a horizontally disposed ring for receiving tension delivering forces or for stabilizing teeth to said ring.

11. A subperiosteal bone anchor as claimed in claim 4, said anchor further including attachment means for attaching an orthodontic appliance to said anchor, said attachment means comprising a stem fixed to said arms, and a tube fixed to said stem.

* * * * *